US008066999B2

(12) United States Patent
DeMattos et al.

(10) Patent No.: US 8,066,999 B2
(45) Date of Patent: Nov. 29, 2011

(54) PEGYLATED Aβ FAB

(75) Inventors: Ronald Bradley DeMattos, Zionsville, IN (US); Jirong Lu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 153 days.

(21) Appl. No.: 12/521,309

(22) PCT Filed: Jan. 9, 2008

(86) PCT No.: PCT/US2008/050554
§ 371 (c)(1),
(2), (4) Date: Jun. 26, 2009

(87) PCT Pub. No.: WO2008/088983
PCT Pub. Date: Jul. 24, 2008

(65) Prior Publication Data
US 2010/0015155 A1 Jan. 21, 2010

Related U.S. Application Data

(60) Provisional application No. 60/885,439, filed on Jan. 18, 2007.

(51) Int. Cl.
*A61K 39/395* (2006.01)
*A61K 39/44* (2006.01)
*C07K 16/18* (2006.01)

(52) U.S. Cl. ............ 424/139.1; 424/133.1; 424/178.1; 530/387.1; 530/387.9; 530/391.1; 530/866

(58) Field of Classification Search .................. None
See application file for complete search history.

(56) References Cited

U.S. PATENT DOCUMENTS

| | | | |
|---|---|---|---|
| 5,004,697 A | 4/1991 | Pardridge | |
| 5,278,049 A | 1/1994 | Baker et al. | |
| 5,593,846 A | 1/1997 | Schenk et al. | |
| 5,688,651 A | 11/1997 | Solomon | |
| 5,753,624 A | 5/1998 | McMichael et al. | |
| 5,766,846 A | 6/1998 | Schlossmacher et al. | |
| 5,837,672 A | 11/1998 | Schenk et al. | |
| 5,851,996 A | 12/1998 | Kline | |
| 5,935,927 A | 8/1999 | Vitek et al. | |
| 6,114,113 A | 9/2000 | McLaughlin-Taylor et al. | |
| 6,114,133 A | 9/2000 | Seubert et al. | |
| 6,218,506 B1 | 4/2001 | Krafft et al. | |
| 6,284,221 B1 | 9/2001 | Schenk et al. | |
| 6,582,945 B1 | 6/2003 | Raso | |
| 7,575,747 B2 * | 8/2009 | Davies et al. ............ | 424/145.1 |
| 2002/0009445 A1 | 1/2002 | Du et al. | |
| 2002/0058267 A1 | 5/2002 | Ozenberger et al. | |
| 2002/0086847 A1 | 7/2002 | Chain | |
| 2002/0102261 A1 | 8/2002 | Raso | |
| 2002/0136718 A1 | 9/2002 | Raso | |
| 2004/0043418 A1 | 3/2004 | Holtzman et al. | |
| 2004/0121415 A1* | 6/2004 | King et al. .................. | 435/7.23 |
| 2004/0192893 A1 | 9/2004 | Stavrianopoulos et al. | |
| 2004/0241164 A1 | 12/2004 | Bales et al. | |
| 2004/0248197 A1 | 12/2004 | Holtzman et al. | |
| 2004/0265308 A1 | 12/2004 | Schenk | |
| 2005/0019330 A1 | 1/2005 | Schenk | |
| 2006/0257396 A1* | 11/2006 | Jacobsen .................... | 424/141.1 |
| 2006/0286066 A1* | 12/2006 | Basran ......................... | 424/85.1 |

FOREIGN PATENT DOCUMENTS

| | | |
|---|---|---|
| EP | 0613007 | 2/1994 |
| EP | 0557270 | 5/1995 |
| EP | 1 257 584 | 2/2001 |
| WO | WO 89/01343 | 2/1989 |
| WO | WO 96/18900 | 6/1996 |
| WO | WO 96/25435 | 8/1996 |
| WO | WO 98/33815 | 8/1998 |
| WO | WO 98/34643 | 8/1998 |
| WO | WO 98/44955 | 10/1998 |
| WO | WO 99/27944 | 6/1999 |
| WO | WO 99/06066 | 11/1999 |
| WO | WO 99/60024 | 11/1999 |
| WO | WO 00/72880 | 12/2000 |
| WO | WO 00/77178 | 12/2000 |
| WO | WO 99/72876 | 12/2000 |
| WO | WO 01/10900 | 2/2001 |
| WO | WO 01/18169 | 3/2001 |
| WO | WO 01/62801 | 8/2001 |
| WO | WO 02/021141 | 3/2002 |
| WO | WO 02/046237 | 6/2002 |
| WO | WO 02/060481 | 8/2002 |
| WO | WO 03/015617 | 2/2003 |
| WO | WO 03/015691 | 2/2003 |
| WO | WO 03/016466 | 2/2003 |
| WO | WO 03/016467 | 2/2003 |
| WO | WO 03/090772 | 11/2003 |
| WO | WO 2004/071408 A2 * | 8/2004 |

OTHER PUBLICATIONS

Bacskai et al. Non-Fc-mediated mechanisms are involved in clearance of amyloid-beta in vivo by immunotherapy. J Neurosci. 2002; 22(18):7873-7878.*
Choy EHS et al. Efficacy of a novel PEGylated humanized anti-TNF fragment (CDP870) in patients with rheumatoid arthritis: a phase II double-blinded, randomized, dose-escalating trial. Rheumatol. 2002; 41(10):1133-1137.*
Holm et al. Mol Immunol. 2007; 44(6):1075-1084.*
Humphreys DP et al. Alternative antibody Fab' fragment PEGylation strategies: combination of strong reducing agents, disruption of the interchain disulphide bond and disulphide engineering. Protein Eng Des Sel. 2007; 20(5):227-234.*
Mitchell et al. Curr Drug Targets. 2007; 8(7):832-838.*
Rudikoff et al. Proc Natl Acad Sci USA, 1982; 79(6):1979-1983.*
Vickers JC. Drugs Aging. 2002; 19(7):487-494.*
Haass, C., et al., "Amyloid beta-peptide is produced by cultured cells during normal metabolism," *Nature*, 359:322-325 (1992).
Ghiso, J., et al., "Epitope map of two polyclonal antibodies that recognize amyloid lesions in patients with Alzheimers disease," Biochem J, 282 (Pt 2):517-522 (1992).
Seubert, P., et al., "Isolation and quantification of soluble Alzheimer's β peptide from biological fluids," *Nature*, 359:325-327 (1992).
Gaskin, F., et al., "Human antibodies reactive with beta-amyloid protein in Alzheimer's disease," *J Exp Med*, 177(4): 1181-1186 (1993).

(Continued)

*Primary Examiner* — Elizabeth C Kemmerer
*Assistant Examiner* — Kimberly A Ballard
(74) *Attorney, Agent, or Firm* — Sanjay M. Jivraj

(57) ABSTRACT

A method to treat conditions associated with Aβ peptide activity both prophylactically and therapeutically is described. The method employs humanized antibody fragments that specifically bind human Aβ peptide between amino acid positions 13-28, wherein the antibody fragments are covalently attached to a polyethylene glycol (PEG) molecule.

3 Claims, No Drawings

OTHER PUBLICATIONS

Flood, JF, et al., "An amyloid β-protein fragment, Aβ [12-28], equipotently impairs post-training memory processing when injected into different limbic system structures," *Brain Res*, 663(2):271-276 (1994).

Koudinov, A., et al., "The soluble form of Alzheimer's amyloid beta protein is complexed to high density lipoprotein 3 and very high density lipoprotein in normal human plasma," *Biochem & Biophysic Res Comm*, 205:1164-1171 (1994).

Schwarzman, AL et al., "Transthyretin sequesters amyloid β protein and prevents amyloid formation," *Proc Nall Acad Sci*, 91:8368-8372, (1994).

Tabaton, M., et al., "Soluble amyloid β-protein is a marker of Alzheimer amyloid in brain but not in cerebrospinal fluid," *Biochem and Biophysi Res Comm*, 200(3)1598-1603 (1994).

Walker, LC et al., "Labeling of cerebral amyloid in vivo with a monoclonal antibody," *J Neuropathol Exp Neurol*, 53(4):377-383 (1994).

Wisniewski, T., et al., "Alzheimer's disease and soluble A beta," *Neurobiol Aging*, 15(2):143-52 Review (1994).

Demattos, R.B., et al., "Brain to Plasma Amyloid-β Efflux: a Measure of Brain Amyloid Burden in a Mouse Model of Alzheimer's Disease," *Science*, 295, pp. 2264-2267 (2002).

Giulian, D., et al., "Specific domains of β-amyloid from Alzheimer plaque elicit neuron killing in human microglia," *J Neutosci*, 16 (19):6021-6037 (1996).

Hanan, E., et al., "Inhibitory effect of monoclonal antibodies on Alzheimer's βamyloid peptide aggregation," *Int J Exp Clin Invest*, 3:130-133 (1996).

Solomon, B., et al., "Monoclonal antibodies inhibit in vitro fibrillar aggregation of the Alzheimer beta-amyloid peptide," *Proc Natl Acad Sci USA*, 93(1):452-5 (1996).

Teller, JK et al., "Presence of soluble amyloid β-peptide precedes amyloid plaque formation in Down's syndrome," *Nature Medicine*, 2(1)93-95 (1996).

Tjernberg, Lo el al., "Arrest of beta-amyloid fibril formation by a pentapeptide ligand," *J Biol Chem*, 271(15):8545-8548 (1996).

Winter G., et al., "Humanized antibodies" *Immunology Today*, 14(6):243-246 (1996).

Solomon, B., et al., "Disaggregation of Alzheimer beta-amyloid by site-directed mAb," *Proc Nat Acad Sci USA*, 94(8):4109-4112 (1997).

El-Agnaf, OM et al., "The influence of the central region containing residues 19-25 on the aggregation properties and secondary structure of Alzheimer's beta-amyloid peptide," *Eur J Biochem*, 256(3):560-569 (1998).

He X-Y et al., "Humanization and pharmacokinetics of a monoclonal antibody with specificity for both E- and P-selectin," *J Immunol*, 160:1029-1035 (1998).

Lambert, MP et al., "Diffusible, nonfibrillar ligands derived from Aβ1-42 are potent central nervous system neurotoxins," *Proc Natl Acad Sci*, 95:6448-6453 (1998).

Solomon, B., et al., The amino terminus of the β-amyloid peptide contains an essential epitope for maintaining its solubility, *Progress in Alzheimer's and Parkinson's Diseases*, 205-211 (1998).

Soto, C., et al., "1-sheet breaker peptides inhibit fibrillogenesis in a rat brain model of amyloidosis: Implications of Alzheimer's therapy," *Nature Medicine*, 4(7):822-826(1998).

Blass, JP, "Immunologic treatment of Alzheimer's disease," *NEJM*, 341:1694-1695 (1999).

Kuo, YM et al., "High levels of circulating Abeta42 are sequestered by plasma proteins in Alzheimer's disease," *Biochem Biophys Res Commun*, 257(3):787-791 (1999).

McLean, C., et al., "Soluble pool of AP amyloid as a determinant of severity of neurodegeneration in Alzheimer's disease," *Amer Neurological Assoc*, 46:860-866 (1999).

Schenk, D., et al., "Immunization with amyloid-β attenuates Alzheimer-disease-like pathology in the PDAPP mouse," *Nature*, 400:173-177 (1999).

St. George-Hyslop, P., et al., "Antibody clears senile plaques" *Nature*, 400:116-117 (1999).

Wang, J., et al., "The levels of soluble versus insoluble brain AP distinguish Alzheimer's disease from normal and pathologic aging," *Experimental Neurology*, 158:328-337 (1999).

Bard, F., et al., "Peripherally administered antibodies against amyloid beta-peptide enter the central nervous system and reduce pathology in a mouse model of Alzheimer disease," *Nat Med*, 6(8):916-919 (2000).

Games, D., et al., "Prevention and reduction of AD-type pathology in PDAPP mice immunized with Aβ$_{1-42}$," *Annals of NY Acad Sci*, 920:274-284 (2000).

Levy A., et al., "Immunization for Alzheimer's disease: A shot in the arm or a whiff?" *American Neurological Assoc*, 48:553-555 (2000).

Janus, C., et al., "Aβ peptide immunization reduces behavioural impairment and Plaques in a model of Alzheimer's disease," *Nature*, 408:979-982 (2000).

Morgan, D., et al., "Aβ peptide vaccination prevents memory loss in an animal model of Alzheimer's disease," *Nature*, 408:982-985 (2000).

Naslund, J., et al., "Correlation between elevated levels of amyloid β peptide in the brain and cognitive decline," *J Am Med Assoc*, 283:1571 (2000).

Zlokovic, B.V., et al., "Clearance of amyloid β-peptide from brain: transport or metabolism?" *Nature Medicine*, 6(7)718-719 (2000).

Arendash, GW, et al., "Behavioral assessment of Alzheimer's transgenic mice following long-term AP3 vaccination: Task specificity and correlations between Aβ deposition and spatial memory," *DNA and Cell Biology*, 20(11):737-744 (2001).

Bacskai, BJ, et al., "Imaging of amyloid-β deposits in brains of living mice permits direct observation of clearance of plaques with immunotherapy," *Nature Medicine*, 7(3):369-372 (2001).

DeMattos, R.B., et al., "Peripheral anti-Aβ antibody alters CNS and plasma AP clearance and decreases brain Aβ burden in a mouse model of Alzheimer's disease," *PNAS*, 98(15):8850-8855 (2001).

Bard, Frederique, et al., "Peripherally administered antibodies against amyloid β-peptide enter the central nervous system and reduce pathology in a mouse model of Alzheimer's disease," *Nature Medicine*, 6(8), 916-919 (2000).

Dickey, CA, el al., Duration and specificity of humoral immune responses in mice vaccinated with the Alzheimer's disease-associated β-amyloid 1-42 peptide, *DNA and Cell Biology*, 20(11):723-729 (2001).

Esiri, MM, et al., "Is an effective immune intervention for Alzheimer's disease in prospect?" *Trends Pharmacol Sci*, 22(1):2-3 (2001).

Haass, C., et al., "Protofibrils, the unifying toxic molecule of neurodegenerative Disorders?" *Nature Neuroscience*, 4(9):859-860 (2001).

Klein, WL, et al., "Targeting small AP oligomers: the solution to an Alzheimer's disease conundrum?" *Trends in Neurosciences*, 24(4):219-224 (2001).

Lambert, MP, et al., "Vaccination with soluble AP oligomers generates toxicityneutralizing antibodies," *J Neurochem*, 79:595L605 (2001).

Lee, VM-Y, et al., "AP immunization: Moving AO peptide from brain to blood," PNAS, 98(16), pp. 8931-8932 (2001).

Poduslo, JF, et al., "Permeability of proteins at the blood-brain barrier in the normal adult mouse and double transgenic mouse model of Alzheimer's disease," *Neurobiol Dis*, 8(4):555-567 (2001).

Town, T., et al., "Characterization of murine immunoglobulin G antibodies against human amyloid-β$_{1-42}$," *Neuroscience Letters*, 307:101-104 (2001).

DeMattos R.B., et al., "Plaque-associated disrupton of CSF and plasma amyloid-P(AP) equilibrium in a mouse model of Alzheimer's disease," *J Neurochem*, 81:229-236, (2002).

Kotilinek, L.A., et al., "Reversible memory loss in a mouse transgenic model of Alzheimer's disease," *J Neurosci*, 22(15):6331-6335 (2002).

Wang, H-W, et al., "Soluble oligomers of β amyloid (1-42) inhibit long-term potentiation but not long-term depression in rate dentate gyrus," *Brain Research*, 924:133-140 (2002).

Strbak, V., et al, "Passive Immunization and Hypothalamic Peptide Secretion," *Neuroendocrinology*, 58:210-217(1993).

Ragusi, C., et al., "Redistribution of Imipramine from Regions of the Brain Under the Influence of Circulating Specific Antibodies," *J. Neurochem.*, 70(5), pp. 2099-2105 (1998).

Suo, Z., et al., "Soluble Alzheimers β-amyloid constricts the cerebral vasculature in vivo" *Neuroscience Letters* 257, pp. 77-80 (1998).
Lue, L., et al., "Soluble β-amyloid Peptide Concentration as a Predictor of Synaptic Change in Alzheimer's Disease," *Am. J PatholL*, 155:pp. 853-862 (1999).
Teller, J., et al., "Presence of soluble amyloid β-peptide precedes amyloid plaque formation in Down's syndrome," *Nature Medicine*, vol. 2, No. 1, pp. 93-95 (1996).
Esler, W., et al., "Point substitution in the central hydrophobic cluster of a human β-amyloid congener disrupts peptide folding and abolishes plaque competence," *Biochemistry*, vol. 35, pp. 13914-13921 (1996).
Maggio, J. & Mantyh, P. "Brain Amyloid—A Physicochemical Perspective" *Brain Pathology*, vol. 6,147-162 (1996).
Gorevic, P., et al. "Ten to fourteen residue peptides of Alzheimer's disease protein are sufficient for amyloid fibril formation and its characteristic X ray diffraction pattern" *Biochem. and Biophy Res. Commun.*, vol. 147, No. 2 (1987).
Balbach, J., et al. "Amyloid fibril formation by $A\beta_{16-22}$, a seven-residue fragment of the Alzheimer's P-amyloid peptide, and structural characterization by solid state NMR" *Biochemistry*, vol. 39, pp. 13748-13759 (2000).
Simmons, L., "Secondary structure of amyloid β peptide correlates with neurotoxic activity In Vitro" *Molecular Pharmacology*, vol. 45, pp. 373-379 (1994).
Wood, A., et al., "Prolines and amyloidogenicity in fragments of the Alzheimer's peptide β/A4", *Biochemistry*, vol. 34, pp. 724-730 (1995).
Xu, S. and Gaskin F. "Increased incidence of anti-β-amyloid autoantibodies secreted by Epstein-Barr virus transformed B cell lines from patients with Alzheimer's disease" *Mechanisms of Ageing and Development*, vol. 94, pp. 213-222 (1997).
Soto, C., et al., "The a-helical to β-strand transition in the amino-terminal fragment of the amyloid f-peptide modulates amyloid formation" *J. Biol. Biol. Chem*, vol. 270, No. 7, pp. 3063-3067 (1995).
Tjernberg, L., et al., "A molecular model for Alzheimer amyloid β-peptide fibril formation," *J Biol. Chem*, vol. 274, No. 18, pp. 12619-12625 (1999).
Hilbich, C., et al., "Substitutions of hydrophobic amino acid reduce the amyloidogenicity of Alzheimer's disease βA4 peptides," *J. Mol. Biol.*, vol. 228, pp. 460-473 (1992).
Hilbich, C., et al., "Human and rodent sequence analogs of Alzheimer's amyloid βA4 share similar properties and can be solubized in buffers of pH 7.4" *Eur. J. Biochem.*, vol. 201, pp. 61-69(1991).
Hilbich, C., et al., "Aggregation and secondary structure of synthetic amyloid βA4 peptides of Alzheimer's disease" *J. Mol. Biol.*, vol. 218, pp. 149-163 (1991).
Pillot, T., et al., "Fusogenic Properties of the C-terminal Domain of the Alzheimer β-Amyloid Peptide" *J. Biol Chem.*, vol. 271, No. 24, pp. 28757-28765 (1996).

Dodart, JC, et al, "Immunization reverses memory deficits without reducing brain Aβ burden in Alzheimer's disease model," *Nature Neuroscience*, vol. 5(5) 452-457 (2002).
Shibata, et al., "Clearance of Alzheimer's Amyloid-$\beta_{1-40}$ peptide from brain by LDL receptor-related protein-lat the blood-brain barrier," *J. Clin. Invest*, 106:1489-1499 (2000).
Zlokovic, et al., "Blood-Brain Barrier Transport of Circulating Alzheimer's," *Biochem. Biophys. Res. Comm.*, 197(3):1034-1040 (1993).
Racke, et al., "Exacerbation of Cerebral Amyloid Angiopathy-Associated Microhemorrahage in amyloid Precursor Protein Transgenic Mice by Immunotherapy Is Dependent on Antibody Recognition of Deposited Forms of Amyloid β," *J. Neurosic.*, 19:25(3):629-636 (2005).
Legleiter, et al., "Effect of Different Anti-Aβ Antibodies on Aβ Fibrillogenesis as Assessed by Atomic force Microscopy," *J. Mol. Biol.* 23:335(4):997-1006 (2004).
Gavel, et al., "Sequence differences between glycosylated and non-glycosylated Asn-X-Thr/Ser acceptor sites: implications for protein engineering," *Protein Engineering*, vol. 3(5), 433-442, (1990).
Co, M.S., et al., "Genetically Engineered Deglycoslation of the Variable Domain Increases The Affinity Of An Anti-CD33 Monoclonal Antibody," *Molecular Immuno.*,vol. 30(15) 1361-1367 (1993).
Wallick, S.C., et al., "Glycosylation of a $V_H$ Residue of a Monoclonal Antibody Against α(1-6) Dextran Increases Its Affinity for Antigen," *J. Exp Med.*, vol. 168, 1099-1109 (1988).
Wright, A., et al., "Antibody variable region glycosylation: position effects on antigen binding and carbohydrate structure," *EMBO Journal*, vol. 10(10) 2727-2723 (1991).
Lee, VM-Y, et al., "Aβ immunization: Moving Aβ peptide from brain to blood," *PNAS*, vol. 98(16) 8931-8932 (2001).
Levitt, M., "Molecular dynamics of native protein," *J Mol Biol*, 168:595-620 (1983).
Queen, C., et al., "A humanized antibody that binds to the interleukin 2 receptor," *Proc Natl Acad Sci USA*, 8610029-1003 (1989).
Burdick, D., et al., "Assembly and aggregation properties of synthetic Alzheimer's A4/β amyloid peptide analogs," *J Biol Chem*, 267:546-55 (1992).
Co, M.S., et al., "Chimeric and humanized antibodies with specificity for the CD33 antigen," *J Immunol*, 148:1149-1154 (1992).
Ghersi-Egea, et al., "Fate of Cerebrospinal Fluid-Borne Amyloid β-Peptide: Rapid Clearance into Blood and Appreciable Accumulation by Cerebral Arteries," *Journal of Neurochemistry*, vol. 67(2), 880-883 (1996).
Kawarabayashi, et al., "Age-Dependent Changes in Brain, CSF, and Plasma Amyloid β Protein in the Tg2576 Transgenic Mouse Model of Alzheimer's Disease," *J. Neuroscience*, 21:372-381 (2001).

* cited by examiner

PEGYLATED Aβ FAB

This application claims priority of the PCT patent application PCT/US2008/050554, filed Jan. 9, 2008, which claims the priority of United States provisional application 60/885,439, filed Jan. 18, 2007. The contents of each of these applications are incorporated herein by reference.

The present invention relates to an antibody fragment that binds amyloid beta (Aβ) peptide and is covalently attached to one or more molecules of polyethylene glycol (PEG).

The Aβ peptide in circulating form is composed of 39-43 amino acids (mostly 40 or 42 amino acids) resulting from the cleavage of a precursor protein, amyloid precursor protein (APP). Conversion of Aβ from soluble to insoluble forms with high β-sheet content and its deposition as neuritic and cerebrovascular plaques in the brain appears to be associated with a number of conditions and diseases, including Alzheimer's disease, Down's syndrome, and cerebral amyloid angiopathy (CAA). Prevention and/or reversal of Aβ deposition may treat conditions associated with the Aβ peptide.

Therapeutic agents that affect Aβ deposition include antibodies to Aβ peptide, such as the humanized antibodies and fragments discussed in WO 2001/62801, WO2004/071408 and Tamura, Y., et al, *Neurobiol. of Dis.* (2005) 20:541-545.

While many antibodies and their derivatives may be useful in diagnosis and therapy, the ideal pharmacokinetics of antibodies often are not achieved for a particular application. Therapeutic antibodies aimed at combating various conditions and diseases associated with Aβ peptide are generally immunoglobulins with intact Fc regions. Fc regions are responsible for prolonging the antibody half-life in the plasma. This prolongation, however, may be a disadvantage as it prevents the antibody that is bound to the target peptide from being effectively cleared, resulting in antigen antibody complex being present in plasma circulation for extended amounts of time. Subsequent administration of the antibody leads to further accumulation of the undesired complex in the plasma. The Fc portion of an antibody may have certain unwanted effector functions and may need to be modified to eliminate such functions. Further, the Fc portion adds substantial size to the overall therapeutic which often creates issues associated with route of delivery, delivery devices, and scale-up manufacturing processes.

Antibody fragments without an Fc portion, including Fabs, have been studied in vivo to determine whether such fragments might be potential therapeutics. Studies suggest, however, that the usefulness of therapies involving fragments such as Fabs is limited due to a fast clearance rate and a short half-life. Therefore, there is a need for an active therapeutic anti-Aβ peptide antibody molecule with pharmacokinetics and pharmacodynamics that allow for an improved dosing regimen while avoiding potential side effects that may be created by complex formation in the plasma and potential effector functions.

The present invention overcomes a number of problems associated with therapeutic antibodies or antibody fragments which may be targeted to Aβ peptide. The compounds of the present invention encompass an antibody fragment that binds Aβ and is covalently attached to one or more molecules of polyethylene glycol (PEG). These compounds can be produced in bacterial or yeast cell systems which eliminate various issues associated with antibody production in mammalian cell lines such as cost issues, purification issues, and contaminating endogenously produced antigen issues. Furthermore, the compounds of the present invention may be administered subcutaneously and have an ideal pharmacokinetics (PK) and pharmacodynamic (PD) profile while preserving affinity and selectivity of the antibody fragment for Aβ.

Quite unpredictably and unexpectedly, applicants also found that covalently attaching PEG molecules to the complementarity determining region (CDR) of the antibody fragment did not alter the activity, affinity or selectivity of the antibody fragment for Aβ.

This invention provides a molecule comprising an antibody fragment that specifically binds human Aβ peptide between amino acid positions 13-28, wherein the antibody fragment is covalently attached to a PEG molecule. Preferably, the antibody fragment is a Fab fragment.

In one embodiment, the invention provides a molecule comprising an antibody fragment that has a heavy chain variable region and a light chain variable region, wherein the light chain variable region comprises CDR regions with the following amino acid sequences: CDRL1: SSSQSLIYSDG-NAYLH (SEQ ID NO: 6), CDRL2: KVSNRFS (SEQ ID NO: 7) and CDRL3: TQSTHSPWT (SEQ ID NO: 8) and wherein the heavy chain variable region comprises CDR regions with the following amino acid sequences: CDRH1: GYTFS-RYSMS (SEQ ID NO: 9), CDRH2: QINIRGCNTYYP-DTVKG (SEQ ID NO: 10) or QINIRGNNTYYPDTVKG (SEQ ID NO: 11), and CDRH3: GDF (SEQ ID NO: 12). Preferably, such a molecule has a PEG molecule that is covalently attached to either the heavy chain variable region or the light chain variable region of the antibody fragment. More preferably, such a molecule has a PEG molecule that is covalently attached to a CDR. Even more preferably, such a molecule has a PEG molecule that is covalently attached to a cysteine residue within the CDR. Most preferably, such a molecule has a PEG molecule that is covalently attached to a CDRH2: QINIRGCNTYYPDTVKG (SEQ ID NO: 10) of the heavy chain variable region of the antibody fragment.

In another embodiment, the invention provides a molecule comprising an antibody fragment that has a light chain variable region of SEQ ID NO: 1, and a heavy chain variable region of SEQ ID NO: 2. Preferably, such a molecule has a PEG molecule that is covalently attached to either the heavy chain variable region or the light chain variable region of the antibody fragment. More preferably, such a molecule has a PEG molecule that is covalently attached to a CDR of a heavy chain variable region of the antibody fragment. Even more preferably, such a molecule has a PEG molecule that is covalently attached to a cysteine residue within the CDR of a heavy chain variable region of the antibody fragment. Most preferably, such a molecule has a PEG molecule that is covalently attached to the cysteine at amino acid position 56 of the heavy chain variable region of SEQ ID NO: 2.

In another embodiment, the invention provides a molecule comprising a Fab fragment or a ScFv fragment, wherein the Fab fragment or ScFv fragment is covalently attached to a PEG molecule and has a light chain variable region of SEQ ID NO: 1, and a heavy chain variable region of SEQ ID NO: 2. Preferably, such a molecule has a PEG molecule that is covalently attached to the cysteine at amino acid position 56 of the heavy chain variable region of SEQ ID NO: 2. Also preferably, in such a molecule the molecular weight of the PEG is about 0.5 kD to about 30 kD, more preferably 20kD.

In another embodiment the invention provides a molecule comprising an antibody fragment with a light chain variable region of SEQ ID NO: 1 and a heavy chain variable region of SEQ ID NO: 2, wherein the said antibody fragment is covalently attached to a 20 kD PEG molecule at position 56 of the heavy chain variable region of the SEQ ID NO: 2. Preferably, in such a molecule the PEG molecule is covalently attached via a maleimide linkage.

In another embodiment the invention provides a molecule comprising an antibody fragment that specifically binds human Aβ peptide between amino acid positions 13-28, wherein the antibody fragment is covalently attached to a PEG molecule and has a light chain variable region of SEQ ID NO: 1, and a heavy chain variable region of SEQ ID NO: 3. Preferably, such a molecule has a PEG molecule that is covalently attached to the hinge region of the antibody fragment. More preferably, the PEG is covalently attached to the hinge region via a maleimide linkage.

The invention also includes a molecule comprising antibody fragments, preferably humanized antibody fragments in which a PEG molecule is covalently attached to the antibody fragment that results in an active therapeutic molecule with pharmacokinetics and pharmacodynamics that allow for weekly dosing regimen, while minimizing potential side effects that may be created by complex formation in the plasma and preserving or improving activity, affinity and selectivity of the antibody fragment for Aβ.

The invention also includes methods of treating, preventing, or reversing conditions and diseases associated with Aβ peptide, including both pre-clinical and clinical Alzheimer's disease, Down's syndrome, and pre-clinical and clinical cerebral amyloid angiopathy (CAA) cognitive deficit, stroke, brain hemorrhage, and general mental debilitation. These methods comprise administering to a subject an effective amount of a molecule described and claimed herein.

This invention provides a molecule comprising an antibody fragment that specifically binds Aβ peptide between amino acid positions 13-28, wherein the antibody fragment is covalently attached to a PEG molecule. We have found that covalently attaching a PEG molecule to an antibody fragment that binds Aβ did not negatively alter the activity, affinity or selectivity of the antibody fragment for Aβ. More surprisingly, we found that covalently attaching a PEG molecule having a molecular weight up to 20 kD to a CDR of an antibody fragment that binds Aβ also did not negatively alter the activity, affinity or selectivity of the antibody fragment for Aβ peptide. These antibody fragments may be administered subcutaneously and have an improved PK/PD profile for therapeutic use supporting a flexible dosing regimen. Moreover, these antibody fragments can be produced in bacterial or yeast cell systems that eliminate various issues associated with full-length antibody production in mammalian cells. The pegylated antibody fragments of this invention offer the opportunity to prevent and treat, both prophylactically and therapeutically, conditions in humans associated with Aβ peptide.

A full-length antibody as it exists naturally is an immunoglobulin molecule comprised of four peptide chains, two heavy (H) chains (about 50-70 kDa when full length) and two light (L) chains (about 25 kDa when full length) interconnected by disulfide bonds. The amino terminal portion of each chain includes a variable region of about 100-110 or more amino acids primarily responsible for antigen recognition. The carboxy-terminal portion of each chain defines a constant region primarily responsible for effector function.

Light chains are classified as kappa or lambda and characterized by a particular constant region. Each light chain is comprised of an N-terminal light chain variable region (herein "LCVR") and a light chain constant region comprised of one domain, CL. Heavy chains are classified as gamma, mu, alpha, delta, or epsilon, and define the antibody's isotype as IgG, IgM, IgA, IgD, and IgE, respectively and several of these may be further divided into subclasses (isotypes) e.g., $IgG_1$, $IgG_2$, $IgG_3$, $IgG_4$, $IgA_1$ and $IgA_2$. Each heavy chain type is characterized by a particular constant region. Each heavy chain is comprised of an N-terminal heavy chain variable region (herein "HCVR") and a heavy chain constant region. The heavy chain constant region is comprised of three domains (CH1, CH2, and CH3) for IgG, IgD, and IgA; and 4 domains (CH1, CH2, CH3, and CH4) for IgM and IgE.

The HCVR and LCVR regions can be further subdivided into regions of hypervariability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein the 3 CDRs of the heavy chain are referred to as "CDRH1, CDRH2, and CDRH3" and the 3 CDRs of the light chain are referred to as "CDRL1, CDRL2 and CDRL3." The CDRs contain most of the residues that form specific interactions with the antigen. The numbering and positioning of CDR amino acid residues within the HCVR and LCVR regions is in accordance with the well-known Kabat numbering convention.

The variable region of each light-heavy chain pair forms an antigen-binding site of the antibody. As used herein, the "antigen-binding portion" or "antigen-binding region" or "antigen-binding domain" or "antigen binding site" refers interchangeably to that portion of an antibody molecule which contains the amino acid residues that interact with an antigen and confer on the antibody its specificity and affinity for the antigen. This antibody portion includes the "framework" amino acid residues necessary to maintain the proper conformation of the antigen-binding residues. Preferably, the framework regions of antibodies of the invention are of human origin or substantially of human origin (at least 80%, 85%, 90%, 95%, 96%, 97%, 98% or 99% of human origin) and follow Kabat numbering. Alternatively, the antigen-binding region can be derived from human sequence.

As used herein, the term "antibody fragment" refers to one or more fragments of an antibody that retain the ability to specifically bind to an antigen (e.g., Aβ.). Examples of molecules encompassed within the term "antibody fragment" of an antibody include (i) a Fab fragment, a monovalent fragment consisting of the VL, VH, CL and CH 1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and (v) a dAb fragment (Ward, et al., (1989) *Nature* 341:544-546), which consists of a VH domain. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) *Science* 242:423-426: and Huston et al. (1988) *Proc. Natl. Acad. Sci. USA* 85:5879-5883). Such single chain antibodies are also intended to be encompassed within the term "antibody fragment". Other forms of single chain antibodies, such as diabodies are also encompassed by the term "antibody fragment". Diabodies are bivalent, bispecific binding proteins in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antibody fragment thereof may be part of a larger immunoadhesion molecule, formed by covalent or noncovalent association of the antibody or antibody fragment with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody fragments, such as Fab and F(ab')$_2$ fragments, can be prepared from whole antibodies using conventional techniques, such as papain or pepsin digestion, respectively, of whole antibodies. Moreover, antibodies, antibody fragments and immunoadhesion molecules can be obtained using standard recombinant DNA techniques, as are well known in the art. Antibodies, antibody fragments and immunoadhesion molecules may or may not be glycosylated and still fall within the bounds of the invention. Preferably, the antibody fragment is a Fab fragment.

The term "humanized antibody" refers to an antibody that is composed partially or fully of amino acid sequences derived from a human antibody germline or a rearranged sequence and made by altering the sequence of an antibody having non-human CDRs. The framework regions of the variable regions may be substituted by corresponding human framework regions. The human framework regions include genomic framework regions, as well as those containing one or more amino acid substitutions. In particular, such substitutions include mutations in which an amino acid at a particular position in the human framework is replaced with the amino acid from the corresponding position of the natural framework for the non-human CDR. For example, a humanized antibody having mouse CDRs may contain one or more substitutions that replace a particular human framework amino acid with the corresponding mouse framework amino acid. References further describing methods involved in humanizing a mouse antibody that may be used are e.g., Queen et al., *Proc. Natl. Acad. Sci. USA* 88:2869, 1991; U.S. Pat. Nos. 5,693,761; 4,816,397; 5,225,539; computer programs ABMOD and ENCAD as described in Levitt, M., *J. Mol. Biol.* 168:595-620, 1983; humanization can be essentially performed following the method of Winter and co-workers (Jones et al., *Nature*, 321:522-525, 1986; Riechmann et al., *Nature*, 332:323-327, 1988; Verhoeyen et al., *Science*, 239:1534-1536, 1988). Preferably, an antibody of the invention is a humanized antibody fragment. More preferably, an antibody of the invention is a humanized antibody fab fragment.

The present invention also includes antibody fragments that are covalently attached to one or more molecules of PEG. It is intended that the term "polyethylene glycol" and "PEG" be used interchangeably and refer to polyethylene glycol or a derivative thereof as known in the art (see, e.g., U.S. Pat. Nos. 5,445,090; 5,900,461; 5,932,462; 6,436,386; 6,448,369; 6,437,025; 6,448,369; 6,495,659; 6,515,100 and 6,514,491). Preferably, PEG is covalently attached to one or more lysine or cysteine residues of the antibody fragment. More preferably, PEG is covalently attached to a one or more lysine or cysteine residues in the heavy chain variable region of the antibody fragment. Even more preferably, PEG is covalently attached to a one or more lysine or cysteine residues within the CDR of the antibody fragment. Most preferably, PEG is attached to a cysteine residue at amino acid position 56 of the heavy chain variable region of the said SEQ ID NO: 2. Alternatively, the PEG molecules may be attached to the antibody fragment via a linker or spacer molecule to the hinge region of the antibody fragment. Addition of linkers and spacer molecules to the hinge regions are well known in the art. Furthermore, a PEG may be covalently attached to modified non-natural amino acids of the antibody fragment by techniques well known in the art.

In its typical form, "PEG" is a linear polymer with terminal hydroxyl groups and has the formula HO—CH$_2$CH$_2$—(CH$_2$CH$_2$O)n-CH$_2$CH$_2$—OH, where n is from about 8 to about 4000. The terminal hydrogen may be substituted with a protective group such as an alkyl or alkanol group (M-PEG). Preferably, PEG has at least one hydroxy group, more preferably it is a terminal hydroxy group. It is this hydroxy group which is preferably activated to react with the peptide. A variety of chemical modifications are used to prepare an active PEG derivative with a functional group, such as active carbonate, active ester, aldehyde, tresylate, or using PEG-propionaldehyde suitable for coupling to a given target molecule. The activated PEG derivative is then covalently linked to a reactive group on the polypeptide drug. There are many forms of PEG useful for the present invention. Numerous derivatives of PEG exist in the art and are suitable for use in the invention. The PEG molecule covalently attached to an antibody fragment of the present invention is not intended to be limited to a particular type or size. The molecular weight of the PEG is preferably from about 0.5 kilodaltons (kD) to about 100 kD and more preferably from about 5 kD to about 30 kD and most preferably from about 1 kD to about 20 kD. PEG may be linear or branched and the anti-Aβ peptide antibody fragment of the invention may have 1, 2, 3, 4, 5 or 6 PEG molecules attached to the peptide. It is most preferable that there be one PEG molecule antibody fragment; however, when more than one PEG molecule per peptide molecule is present, it is preferred that there are no more than six. It is further contemplated that both ends of the PEG molecule may adapted for cross-linking two or more anti-Aβ peptide antibody fragment molecules together. Methods of attaching PEG molecules to proteins, antibodies and fragments thereof, are well known in the art.

The term "K$_D$", as used herein, is intended to refer to the dissociation constant of a particular antibody-antigen interaction. It is calculated by the formula:

$$K_D = k_{off}/k_{on} \text{ (measured in M)}$$

The term "k$_{on}$" as used herein is intended to refer to the association rate constant, or specific reaction rate, of the forward, or complex-forming, reaction, measured in units: M$^{-1}$sec$^{-1}$. The term "k$_{off}$", as used herein, is intended to refer to the dissociation rate constant, or specific reaction rate, for dissociation of an antibody from the antibody/antigen complex, measured in units: sec$^{-1}$.

The term "specifically binds" as used herein refers to the situation in which one member of a specific binding pair does not significantly bind to molecules other than its specific binding partner(s). The term is also applicable where e.g., an antigen-binding domain of an antibody of the invention is specific for a particular epitope that is carried by a number of antigens, in which case the specific antibody carrying the antigen-binding domain will be able to bind to the various antigens carrying the epitope. Accordingly, a molecule of the invention specifically binds Aβ peptide while it does not specifically bind APP. Furthermore, a molecule of the invention specifically binds between a linear, non-linear or conformational Aβ epitope comprising amino acids HHQKLVF-FAEDVGSNK (13-28) (SEQ ID NO: 4).

The term "activity" in reference to a molecule of the present invention includes but is not limited to, epitope/antigen affinity and specificity, ability to neutralize or antagonize an activity of Aβ peptide in vivo or in vitro, $IC_{50}$, in vivo stability of the antibody and the immunogenic properties of the antibody. Other identifiable biological properties or characteristics of an antibody recognized in the art include, for example, cross-reactivity, (i.e., with non-human homologs of the targeted peptide, or with other proteins or tissues, generally), and ability to preserve high expression levels of protein in mammalian cells. The aforementioned properties or characteristics can be observed, measured or assessed using art-recognized techniques including, but not limited to, ELISA, competitive ELISA, Biacore or KinExA surface plasmon resonance analysis, in vitro or in vivo neutralization assays without limit, receptor binding, cytokine or growth factor production and/or secretion, signal transduction and immunohistochemistry with tissue sections from different sources including human, primate, or any other source.

The terms "individual," "subject," and "patient," used interchangeably herein, refer to a mammal, preferably human. In a certain embodiment, the subject is further characterized with a disease or disorder or condition that would benefit from a decreased activity of Aβ peptide.

As used herein, the expressions "host cell," "host cell line," and "host cell culture" are used interchangeably and include an individual cell or cell culture that is a recipient of any isolated polynucleotide of the invention or any recombinant vector(s) comprising a sequence encoding a HCVR, LCVR or monoclonal antibody of the invention. Host cells include progeny of a single host cell. The progeny may not be completely identical, in morphology or in total DNA complement, to the original parent cell due to natural, accidental, or deliberate mutation and/or change. A host cell includes cells transformed, transduced or infected with a recombinant vector or a polynucleotide expressing an antibody fragment of the invention or a light chain or heavy chain thereof A host cell which comprises a recombinant vector of the invention, either stably incorporated into the host chromosome or not, may also be referred to as a "recombinant host cell". Preferred cells for generating host cells of the invention are CHO cells (e.g., ATCC CRL-9096), NSO cells, SP2/0 cells, COS cells (ATCC e.g., CRL-1650, CRL-1651) and HeLa (ATCC CCL-2). Additional host cells for use in the invention include plant cells, yeast cells, other mammalian cells and prokaryotic cells. More preferably, the cells for use in the invention are yeast or prokaryotic cells.

The term "condition or disease related to Aβ peptide" or "conditions associated disease with Aβ activity" is meant to include all conditions, disorders and diseases that are associated with: 1) the development of β-amyloid plaques in the brain, 2) the synthesis of abnormal forms of Aβ, 3) the formation of particularly toxic forms of Aβ, or 4) abnormal rates of synthesis, degradation, or clearance of Aβ. Conditions and diseases such as Alzheimer's disease, Down's syndrome, cerebral amyloid angiopathy, certain vascular dementias, and mild cognitive impairment are known or suspected of having such a relationship to Aβ.

This invention provides a molecule comprising an antibody fragment that specifically binds Aβ peptide between amino acid positions 13-28, wherein the antibody fragment is covalently attached to a PEG molecule. The antibody fragment is preferably a humanized antibody fragment, such as a Fab fragment and/or scFv fragment. Most preferably the antibody fragment is a Fab fragment. Specific binding of the molecules of the invention to Aβ peptide allows said molecules to be used as a therapeutic for Aβ peptide associated diseases and disorders, i.e., conditions, diseases or disorders which benefit from inhibition of an Aβ peptide biological activity.

In one embodiment of the invention, the antibody fragment has a heavy chain variable region and a light chain variable region, wherein the light chain variable region comprises CDR regions with the following amino acid sequences: CDRL1: SSSQSLIYSDGNAYLH (SEQ ID NO: 6), CDRL2: KVSNRFS (SEQ ID NO: 7) and CDRL3: TQSTH-SPWT (SEQ ID NO: 8) and/or wherein the heavy chain variable region comprises CDR regions with the following amino acid sequences: CDRH1: GYTFSRYSMS (SEQ ID NO: 9), CDRH2: QINIRGCNTYYPDTVKG (SEQ ID NO: 10) or QINIRGNNTYYPDTVKG (SEQ ID NO: 11), and CDRH3: GDF (SEQ ID NO: 12). Preferably, the six CDRs of an antibody fragment of the invention exist together. The composition comprising a CDR of the invention will generally be an antibody heavy or light chain sequence or a substantial portion thereof, in which the CDR is located at a location consistent with Kabat numbering. The three CDR regions for each chain, heavy and light, are provided in a framework region as a contiguous sequence represented by the following formula: FR1-CDR1-FR2-CDR2-FR3-CDR3-FR4. The heavy chain or light chain FR1, FR2, FR3 and FR4 combine to form the complete framework region of an antibody fragment when arranged as a contiguous sequence with the CDRs in the order stated. Preferably, the framework regions of an antibody of the invention are of human origin or substantially of human origin (i.e., greater than about 80, 82, 85, 87, 90, 92, 95, 97%).

Preferably, the antibody fragment of the invention comprises a LCVR comprising a peptide of the following sequence:

```
                                          (SEQ ID NO: 1)
DIVMTQTPLSLSVTPGQPASISCSSSQSLIYSDGNAYLHWYLQKP

GQSPQLLIYKVSNRFSGVPDRFSGSGSGTDFTLKISRVEAEDVG

VYYCTQSTHSPWTFGGGTKVEIK
``` and a HCVR comprising a peptide with a sequence selected from the group consisting of the following sequences;

```
                                          (SEQ ID NO: 2)
EVQLVESGGGLVKPGGSLRLSCAASGYTFSRYSMSWVRQAPG

KGLEWVGQINIRGCNTYYPDTVKGRFTISRDDSKNTLYLQMNS

LKTEDTAVYYCTTGDFWGQGTLVTVSS (SEQ ID NO: 3)
EVQLVESGGGLVKPGGSLRLSCAASGYTFSRYSMSWVRQAPG

KGLEWVGQINIRGNNTYYPDTVKGRFTISRDDSKNTLYLQMNS

LKTEDTAVYYCTTGDFWGQGTLVTVSS
```

Alternatively, the antibody fragment comprises a LCVR comprising a peptide with a sequence consisting of SEQ ID NO: 1 and a HCVR comprising a peptide with a sequence selected from the group consisting of SEQ ID NO: 2 or SEQ ID NO: 3, wherein the HCVR and LCVR exist together in an antibody fragment. The skilled artisan will appreciate that the antibody fragments of the invention are not limited to the specific sequences of HCVR and LCVR, but also include variants of these sequences that, when present in a molecule of the invention, retain or improve upon antigen binding ability and at least one other functional property of the parent antibody, e.g., epitope specificity, ability to compete with the parent antibody for binding to Aβ peptide, $IC_{50}$ and/or $K_D$ or $k_{off}$ values for binding Aβ peptide.

In another embodiment of the invention, all or a portion of the variable region is limited by a particular LCVR sequence as shown by a SEQ ID NO: 1 and HCVR as shown in SEQ ID NO: 2 or SEQ ID NO: 3 and is further characterized by that it antagonizes or neutralizes at least one Aβ peptide activity in vivo or in vitro. An antibody of the invention, wherein all or a portion of the variable region is limited by a particular sequence as shown by a LCVR SEQ ID NO: 1 and HCVR SEQ ID NO: 2 or SEQ ID NO: 3 herein is further characterized by specifically binding human Aβ peptide but not binding human APP.

In one aspect of the present invention, PEG (or a derivative thereof) is covalently attached to one or more lysine, cysteine or non-natural modified amino acid residues of an antibody fragment. Preferably, the PEG molecule is covalently attached to either the heavy chain variable region or the light chain variable region of the antibody fragment. More preferably, such a molecule has a PEG molecule that is covalently attached to a CDR of a heavy chain variable region of the antibody fragment. Most preferably, such a molecule has a PEG molecule that is covalently attached to the cysteine at amino acid position 56 of the heavy chain variable region of SEQ ID NO: 2. Alternatively, the PEG molecules may be attached to the anti-Aβ peptide Fab antibody fragment via a linker or spacer molecule to the hinge region of the antibody fragment.

In another aspect of the present invention, a PEG molecule is covalently attached to one or more engineered lysine, cysteine or non-natural modified amino acid residues of the antibody of the present invention to replace a gyclosylation present on the antibody molecules without significantly affecting affinity and selectivity of the antibody fragment for Aβ. Preferably, the PEG molecule replaces the gylcosylation signal on the heavy chain variable region or the light chain variable region of the antibody fragment. More preferably, the PEG molecule replaces the glycosylation signal on the CDR of a heavy chain variable region of the antibody fragment. Most preferably, the PEG molecule replaces the gylcosylation signal at position 56 of the heavy chain variable region of SEQ ID NO: 2.

The PEG molecule covalently attached to an antibody in the present invention is not intended to be limited to a particular type or size. PEG's molecular weight is preferably from about 0.5 kD to about 100 kD, and more preferably from about 0.5 kD to about 30 kD, and most preferably from about 1 kD to about 20 kD. Alternatively the molecular weight of the PEG may be selected from a group consisting of about 0.5 kD, about 1 kD, about 5 kD, about 10 kD and about 20 kD. PEG may be linear or branched and the PEGylated anti-Aβ peptide antibody of the invention may have more than one PEG molecules attached to the peptide. Preferably, there is one PEG molecule per PEGylated anti-Aβ peptide antibody.

Most preferably, the antibody molecule of this invention comprises an antibody fragment with a light chain variable region of SEQ ID NO: 1 and a heavy chain variable region of SEQ ID NO: 2, wherein the said antibody fragment is covalently attached to a 20 kD PEG molecule at position 56 of the heavy chain variable region of the SEQ ID NO: 2.

The antigenic Aβ peptide epitope between which the antibodies of the invention bind is a linear, non-linear or conformational epitope that comprises amino acids HHQKLVFFAEDVGSNK (SEQ ID NO: 4). Antibodies which bind said epitope, specifically and preferentially bind Aβ peptide as compared to their binding APP. The monoclonal antibodies of the invention bind Aβ peptide at least 2, 5, 10, 20, 30, 40, 50, 60, 70, 80, 90, or 100-fold greater (e.g., greater affinity or greater specificity) than with which it binds human APP; more preferably at least 150, 200, 250, 300, 350, 400, 450, 500, 550 or 600-fold greater than with which it binds APP, even more preferably it does not bind APP at levels greater than background levels as determined e.g., by ELISA assay, competition ELISA assay or $K_D$ values in a Biacore or KinExA assay.

The antibody fragments of the invention bind an epitope between amino acids HQKLVFFAEDVGSNK (SEQ ID NO: 5) at least 2, 5, 10, 20, 30, 40, 50, 60, 70, 80, 90, or 100-fold greater (e.g., greater affinity or greater specificity) than an epitope not comprising amino acids HQKLVFFAEDVGSNK (SEQ ID NO: 5). More preferably, at least 150, 200, 250, 300, 350, 400, 450, 500, 550 or 600-fold greater than with an epitope not comprising amino acids HQKLVFFAEDVGSNK (SEQ ID NO: 5), even more preferably it does not bind an epitope not comprising amino acids HQKLVFFAEDVGSNK (SEQ ID NO: 5) at levels greater than background levels as determined e.g., by ELISA assay, competition ELISA assay or $K_D$ values in a Biacore or KinExA assay.

In a preferred embodiment, the invention provides an antibody fragment that possesses a strong binding affinity for Aβ peptide, i.e., binds Aβ peptide, or a portion thereof comprising the sequence HQKLVFFAEDVGSNK (SEQ ID NO: 5) [i.e., antibody contacts the HQKLVFFAEDVGSNK polypeptide], with a binding affinity ($K_D$) for human Aβ peptide of less than about 200 pM, 100pM, 50 pM, 40 pM or 30 pM, preferably less than about 20 pM as measured by the KinExA method. Alternatively, the binding affinity ($K_D$) for human Aβ peptide is between 0.1 pM-200 pM. Antibody affinities may be determined as described in the examples herein below or other methods available in the art.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. More preferably, the route of administration of an antibody of the present invention is via subcutaneous injection. Suitable vehicles for such injections are straightforward in the art.

The antibody fragment of the present invention has a shorter half-life than corresponding anti-Aβ peptide full-length antibody in the plasma and is cleared more rapidly from the plasma than the corresponding anti-Aβ peptide full-length antibody. Alternatively, the antibody of the present invention has a longer plasma half life than the corresponding anti-Aβ peptide Fab fragment that is not covalently attached to a PEG molecule, and is cleared less rapidly from the plasma than the corresponding anti-Aβ peptide Fab fragment that is not covalent attached to a PEG molecule (Examples 1, 2 and 3). The term "corresponding" in reference to an antibody as used herein refers to an antibody with the same LCVR and HCVR. For example, the corresponding full-length antibody in reference to an antibody Fab fragment having a LCVR of SEQ ID NO: 1 and a HCVR consisting of SEQ ID NO: 2 would have the same LCVR of SEQ ID NO: 1 and a HCVR consisting of SEQ ID NO: 2 together with an intact Fc domain.

In another aspect, the present invention is directed to recombinant polynucleotides encoding antibodies which, when expressed, comprises the LCVR of SEQ ID NO: 1 and a HCVR consisting of SEQ ID NO: 2. Due to codon degeneracy, other polynucleotide sequences can be readily substituted for those sequences. Particularly preferred polynucleotides of the present invention encode antibodies, which when expressed, comprise the light chain CDRs of SEQ ID NO: 6-8, and heavy chain CDRs of SEQ ID NO: 9, 10 or 11, and 12, or any of the variable regions of SEQ ID NO: 1-SEQ ID NO: 3. Examples of polynucleotide sequences that code for LCVR of SEQ ID NO: 1 and HCVR of SEQ ID NO: 2 are represented in SEQ ID NO: 13 (LCVR) and SEQ ID NO: 14 (HCVR), respectively.

The polynucleotides will typically further include an expression control polynucleotide sequence operably linked to the humanized immunoglobulin coding sequences, including naturally-associated or heterologous promoter regions. Preferably, the expression control sequences will be eukaryotic promoter systems in vectors capable of transforming or transfecting eukaryotic cells, but control sequences for prokaryotic cells may also be used. Once the vector has been incorporated into the appropriate host cell line, the host cell is propagated under conditions suitable for expressing the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired antibodies or antibody fragments can be formed from a variety of different polynucleotides (genomic or cDNA, RNA, synthetic oligonucleotides, etc.) and components (e.g., V, J, D, and C regions), using any of a variety of well-known techniques. Joining appropriate genomic and synthetic sequences is a common method of production, but cDNA sequences may also be utilized.

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

In addition to the humanized antibodies or antibody fragments specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized antibodies of the present invention. In general, modifications of the genes may be readily accomplished by a variety of well-known techniques, such as site-directed mutagenesis.

As stated previously, the polynucleotides will be expressed in hosts after the sequences have been operably linked to (i.e., positioned to ensure the functioning of) an expression control sequence. These expression vectors are typically replicable in the host cells either as episomes or as an integral part of the host chromosomal DNA. Commonly, expression vectors will contain selection markers, e.g., tetracycline or neomycin, to permit detection of those host cells transformed with the desired DNA sequences. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the polynucleotide sequences of interest (e.g., the heavy and light chain encoding sequences and expression control sequences) can be transferred into the host cell by well-known methods, which vary depending on the type of cell. A variety of hosts may be employed to express the antibodies of the present invention using techniques well known in the art. Preferred cell lines include COS, CHO, SP2/0, NSO (available from public repositories such as ATCC, American Type Culture Collection, Manassas, Va.) and yeast cell lines. Preferably, a host cell of the invention comprises one or more vectors or constructs comprising a nucleic acid molecule of the present invention. The host cell of the invention is a cell into which a vector of the invention has been introduced, said vector comprising a polynucleotide encoding a LCVR of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably linked to a promoter sequence. The cell types include mammalian, bacterial, plant and yeast cells. Preferably, the cell is a CHO cell, a COS cell, a SP2/0 cell, a NS0 cell, a yeast cell or a derivative or progeny of any preferred cell type.

Once expressed, the intact antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90%, 92%, 94% or 96% homogeneity are preferred, and 98 to 99% or more homogeneity most preferred, for pharmaceutical uses. Once purified, partially or to homogeneity as desired, the peptides may then be used therapeutically or prophylactically, as directed herein.

A number of symptoms that result in cognitive deficits, stroke, brain hemorrhage, and general mental debilitation appear to be associated with neuritic and cerebrovascular plaques in the brain containing the Aβ peptide. Among these conditions are both pre-clinical and clinical Alzheimer's disease, Down's syndrome, and pre-clinical and clinical cerebral amyloid angiopathy (CAA). The amyloid plaques are formed from Aβ peptide. These peptides circulate in the blood and in the cerebrospinal fluid (CSF), typically in complexed form with lipoproteins. The Aβ peptide in circulating form is composed of 39-43 amino acids (mostly 40 or 42 amino acids) resulting from the cleavage of a common precursor protein, amyloid precursor protein, often designated APP. Some forms of soluble Aβ are themselves neurotoxic and may determine the severity of neurodegeneration and/or cognitive decline (McLean, C. A., et al., *Ann. Neurol.* (1999) 46:860-866; Lambert, M. P., et al. (1998) 95:6448-6453; Naslund, J., J. Am. Med. Assoc. (2000) 283:1571).

Therefore, a pharmaceutical composition comprising a molecule of the invention may be useful for the treatment or prevention of conditions wherein the presence of Aβ peptide causes or contributes to undesirable pathological effects or decrease of Aβ peptide activity has a therapeutic benefit in mammals, preferably humans, including, but not limited to, clinical or pre-clinical Alzheimer's disease, Down's syndrome, clinical or pre-clinical amyloid angiopathy (CAA), prodromal Alzheimer's, mild cognitive impairment (MCI) and cognitive deficits, stroke, brain hemorrhage, and general mental debilitation appear to be associated with neuritic and cerebrovascular plaques in the brain containing the Aβ peptide. The use of a molecule of the present invention for treating or preventing of at least one of the aforementioned disorders in which Aβ peptide activity is detrimental or which benefits for decreased levels of bioactive Aβ peptide is contemplated herein. Additionally, the use of a molecule of the present invention for use in the manufacture of a medicament for the treatment of at least one of the aforementioned disorders is contemplated.

As used herein, the terms "treatment", "treating", and the like, refer to obtaining a desired pharmacologic and/or physiologic effect. The effect may be a partial or complete cure for a disease and/or adverse affect attributable to the progression of the disease. "Treatment", as used herein, includes administration of a compound, particularly to a human, and includes: (a) inhibiting the disease, i.e., arresting its development; or (b) relieving the disease, i.e., causing regression of the disease or disorder or alleviating symptoms or complications thereof. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation.

A molecule of the invention can be incorporated into pharmaceutical compositions suitable for administration to a subject. The molecules of the invention may be administered alone or in combination with a pharmaceutically acceptable carrier, diluent, and/or excipient, in single or multiple doses. The pharmaceutical compositions for administration are designed to be appropriate for the selected mode of administration, and pharmaceutically acceptable diluent, carrier, and/ or excipients such as dispersing agents, buffers, surfactants, preservatives, solubilizing agents, isotonicity agents, stabilizing agents and the like are used as appropriate (See, e.g., Example 14 herein). Said compositions are designed in accordance with conventional techniques as in e.g., *Remington, The Science and Practice of Pharmacy,* 19$^{th}$ Edition, Gennaro, Ed., Mack Publishing Co., Easton, Pa. 1995 which provides a compendium of formulation techniques as are generally known to practitioners.

A pharmaceutical composition comprising a molecule of the present invention can be administered to a subject at risk for or exhibiting pathologies as described herein using standard administration techniques including oral, intravenous, intraperitoneal, subcutaneous, pulmonary, transdermal, intramuscular, intranasal, buccal, sublingual, or suppository administration. Preferably, a molecule of the present invention can be administered to a subject at risk for or exhibiting pathologies as described herein by subcutaneous administration.

A pharmaceutical composition of the invention preferably is a "therapeutically effective amount" or a "prophylactically effective amount" of a molecule of the invention. A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effect of the molecule, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically-effective or prophylactically effective amount is at least the minimal dose, but less than a toxic dose, of an active agent which is necessary to impart therapeutic benefit to a subject. Stated another way, a therapeutically-effective amount of a molecule of the invention is an amount which in mammals, preferably humans, decreases Aβ peptide activity, e.g., binding to Aβ peptide, wherein the presence of Aβ peptide causes or contributes to undesirable pathological effects or decrease in Aβ peptide results in a beneficial therapeutic effect in a mammal, preferably a human.

The route of administration of a molecule of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Subcutaneous injection is most preferred. Suitable vehicles for such injections are straightforward in the art.

The pharmaceutical composition typically must be sterile and stable under the conditions of manufacture and storage in the container provided, including e.g., a sealed vial or syringe. Therefore, pharmaceutical compositions may be sterile filtered after making the formulation, or otherwise made microbiologically acceptable. A typical composition for intravenous infusion could have a volume as much as 250-1000 ml of fluid, such as sterile Ringer's solution, physiological saline, dextrose solution and Hank's solution and a therapeutically effective dose, (e.g., 1 to 100 mg/ml, or more) of the therapeutic agent to deliver the typical dosages listed below. Dose may vary depending on the type and severity of the disease. As is well known in the medical arts, dosages for any one subject depends upon many factors, including the patient's size, body surface area, age, the particular compound to be administered, sex, time and route of administration, general health, and other drugs being administered concurrently. A typical dose can be, for example, in the range of 0.001 to 1000 μg; however, doses below or above this exemplary range are envisioned, especially considering the aforementioned factors. The daily parenteral dosage regimen can be about 0.1 μg/kg to about 100 mg/kg of total body weight, preferably from about 0.3 pg/kg to about 10 mg/kg and more preferably from about 1 μg/kg to 1 mg/kg, even more preferably from about 0.5 to 10 mg/kg body weight per day. Progress may be monitored by periodic assessment. For repeated administrations over several days or longer, depending on the condition, the treatment is repeated until a desired suppression of disease symptoms occurs. However, other dosage regimens may be useful and are not excluded herefrom. The desired dosage can be delivered by a single bolus administration, by multiple bolus administrations, or by continuous infusion administration of the molecule, depending on the pattern of pharmacokinetic decay that the practitioner wishes to achieve.

These suggested amounts of the molecules of the invention are subject to a great deal of therapeutic discretion. The key factor in selecting an appropriate dose and scheduling is the result obtained. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners.

Therapeutic agents of the invention may be frozen or lyophilized for storage and reconstituted in a suitable sterile carrier prior to use. Lyophilization and reconstitution can lead to varying degrees of antibody activity loss. Dosages may have to be adjusted to compensate.

The following examples are intended to illustrate but not to limit the invention. The examples herein below employ, among others, a murine monoclonal antibody designated "266" (m266) which was originally prepared by immunization with a peptide composed of residues 13-28 of human Aβ peptide and a Fab fragment of the murine monoclonal antibody designated 266 (m266-Fab). The antibody is confirmed to immunoreact with this peptide. The preparation of m266 has been described previously. To covalently attach a PEG molecule to m266-Fab, the Fab may be mutated to introduce a cysteine residue in CDR2 (N56C) of the heavy chain variable and PEGylated in a manner shown below (Example 4). As the examples here describe experiments conducted in murine systems, the use of murine monoclonal antibodies is satisfactory. However, in the treatment methods of the invention intended for human use, humanized forms of the antibodies of the present invention, or fragments thereof, are preferred. The 1A1-Fab referred to in the examples below is a humanized antibody Fab fragment that comprises LCVR of SEQ ID NO: 1 and HCVR of SEQ ID NO: 2.

EXAMPLE 1 m266-Fab PEG Subcutaneous PK/PD Studies in PDAPP Mice

Young (3-month-old) transgenic PDAPP mice are used in order to investigate the pharmacokinetic/pharmacodynamic plasma response of antibody and antibody-Aβ complex. Several antibodies are investigated including mouse 266 Fab (m266-Fab), m266-Fab+SKD PEG, m266-Fab+10KD PEG, m266-Fab+20KD PEG, and intact full length m266 IgG antibody. PDAPP+/− mice are injected subcutaneously with 1 mg/kg of antibody and plasma is subsequently isolated at the following time points: 1, 4, 8, 24, 48, 96, 168, and 240 hours post dose. Animals receiving the m266-Fab antibody are analyzed with additional early time points due to the quick turnover of this moiety. The time points for the m266-Fab are as follows: 1, 4, 8, 12, 16, 24, and 48 hours post dose. A total of five animals are analyzed per antibody per time point. Whole blood is obtained via cardiac puncture with 23-gauge needles connected to 1 CC syringes that had previously been rinsed with 0.5 M EDTA. Blood samples are incubated on ice during the isolation procedure and subsequently centrifuged at 14,000 RPM in a refrigerated microcentrifuge at 4-degrees for 15 minutes. The resulting plasma samples are aliquoted and stored at −80-degrees.

A. Methodology for Fab PK Analyses

Plasma Fab concentrations are determined using an antigen capture ELISA. Briefly, the plates are coated with AB-BSA conjugate overnight at 4° C. or 1 hour at 37° C. then blocked with Pierce casein buffer. Standards, control samples, and study samples are added to the plates followed by one hour incubation at room temperature. A goat anti mouse HRP is used for detection and a colorimetric response is developed with OPD substrate. Plates are read at an absorbance of A493 with a reference of A700. Concentrations of immunoreactivity from plasma samples are determined from standard curves prepared from known amounts of m266 Fab in mouse plasma using a 4/5-parameter algorithm. The assay range for the m266 Fab is 0.05 to 0.5 μg/mL. The range for the PEGylated Fabs is 0.075 to 0.8 μg/mL.

The concentrations of immunoreactivity from plasma samples is determined from standard curves prepared from known amounts of m266 Fab in mouse plasma using a 4/5-parameter algorithm. The assay range for the 266 Fab is 0.05 to 0.5 μg/mL. The range for the PEGylated Fabs is 0.075 to 0.8 μg/mL. Results clearly demonstrate that addition of a PEG molecule and increasing the size of the PEG molecule increase the retention of the Pegylated Fabs in the plasma (2545 ng/ml after 8 hours for 20K Pegylated m266-Fab) as compared to the non-Peglylated m266-Fabs (350 ng/ml after 8 hours).

B. m266 Aβ ELISA Assay

In order to measure the amount of plasma Aβ either in the absence or presence of therapeutic antibody (full length or Fab fragment) an ELISA assay is developed and utilized. The Aβ peptides being measured in these assays are full length Aβ1-40 or Aβ1-42. 96 well Immulon 4HBX 96 well ELISA plates (ThermoLabsystems) are coated over night at 4-degrees with the C-terminal capture antibody (m2G3 for Aβ40 plates or m21F12 for Aβ42 plates) at 10 μg/ml in PBS (100 μl per well). Test plates are sealed to prevent evaporation during the overnight incubation. The following day, well-solution is removed and the wells are washed three times with PBS (400 μl per well) with a Labsystems 96-Well Plate washer. Blocking buffer (360 μl of 1% milk-PBS) is added and plates incubated at 37 degrees for one hour. Samples are prepared by diluting plasma into the sample diluents to yield the following: 20% plasma, 0.5 M guanidine, 5 mM Tris pH 8.0, 0.5× protease inhibitor cocktail, 25 μg/ml m266, and PBS. The volume of plasma used in the assay may need to be decreased for certain time points due to the high levels of Aβ peptide present, and in these instances, the residual plasma volume is adjusted with rat plasma (final percent volume is maintained at 20%). The Aβ standards with concentrations varying from 250 pg/ml to 3.9 pg/ml are generated in standard diluent (20% rat plasma, 0.5 M guanidine, 5 mM Tris pH 8.0, and 0.5× protease inhibitor cocktail Complete EDTA-free (Roche Diagnostics), 25 μg/ml m266, and PBS). The incorporation 25 μg/ml of intact m266 in both sample and standard diluents is required in order to neutralize any negative interference that the variable levels of the central domain antibodies may exert in the assay. After blocking, the plates are washed 4 times with PBS. Samples and standards are loaded in triplicate (100 μl per well) and the plate is sealed and incubated overnight at 4 degrees. The following morning, the plates are washed 4 times with PBS-T (PBS+0.05% Tween-20) and the wells incubated with the biotinylated secondary antibody m3D6 (100 μl per well diluted in 0.5% BSA/PBS-T) for 2 hours at room temperature. After the plates are washed 4 times with PBS-T, they are incubated with streptavidin-poly-HRP (1:5000 in 0.5% BSA/PBS-T) for 1.5 hours at room temperature. The plates are washed 4 times with PBS-T and 100 μl per well of TMB (Sigma) substrate is added. The colorimetric progression is monitored at 650 nm at 15, 30, and 60 minutes.

TABLE 1

Pharmacodynamic Results:
Average Plasma Concentration for Aβ 40 (pg/ml)

| Time (h) | m266 Fab | m266 Fab + 5KD PEG | m266 Fab + 10KD PEG | m266 Fab + 20KD PEG | m266 Intact |
|---|---|---|---|---|---|
| 1 | 246.7 | 253.5 | 178.4 | 196.3 | 223.7 |
| 4 | 498.8 | 693.2 | 898.1 | 816.6 | 1110 |
| 8 | 576.7 | 997.8 | 1011 | 1259 | 1852 |
| 12 | 530.9 | | | | |
| 18 | 344.1 | | | | |
| 24 | 181.2 | 914.7 | 1728 | 2966 | 6919 |
| 48 | | 200.1 | 789.6 | 2642 | 8557 |
| 96 | | 79.1 | 104.8 | 329.3 | 10792 |
| 168 | | 62.64 | 76.49 | 143.3 | 9923 |
| 240 | | 50.14 | 98.24 | 101.2 | 6114 |

In addition to a more flexible dosing schedule which can be manipulated based on the size of PEG, the results demonstrate that the PEGylated Fab-antigen complex does not accumulate in plasma circulation for extended amounts of time like the intact antibody (m266 intact). The intact antibody prolongs the antibody half-life in the plasma and results in the antigen:antibody complex being present in plasma circulation for extended amounts of time (>240 hours). The native Fabs (m266 Fab) on the other hand have a rapid clearance rate and a short half-life (<24 hours) which limit their as a therapy. In contrast, as demonstrated in Table 1, the Pegylated Fabs provide an antibody molecule with pharmacokinetics and pharmacodynamics that allow for improved dosing regimen.

EXAMPLE 2

1A1-Fab PEG Subcutaneous PK/PD Studies in PDAPP Mice

Studies are performed in young (3-month-old) transgenic PDAPP mice in order to investigate the pharmacokinetic/pharmacodynamic plasma response of antibody and antibody-Aβ complex. Several antibodies are investigated including humanized 1A1-Fab, 1A1-Fab+SKD PEG, 1A1-Fab+10KD PEG, and 1A1-Fab+20KD PEG. PDAPP+/− mice are injected subcutaneously with 1 mg/kg of antibody and plasma is subsequently isolated at different time points depending upon antibody injection group. The following time points are used for the various antibodies:

1A1-Fab are bled at 1, 4, 8, 12, 18, 24, and 48 hours post dose

1A1-Fab+5KD PEG are bled at 1, 4, 8, 24, 48, 96, and 168 hours post dose

1A1-Fab+10KD PEG are bled at 1, 4, 8, 24, 48, 96, and 168 hours post dose

1A1-Fab+20KD PEG are bled at 1, 8, 24, 48, 96, 168, and 240 hours post dose

A total of five animals are analyzed per antibody per time point. The resulting plasma samples are aliquoted and stored at −80-degrees.

A. Methodology for Fab PK Analysis

Plasma 1A1 Fab concentrations for 1A1 Fab are determined using a sandwich ELISA. Plates are coated with goat anti-human IgG Kappa standards, control samples, and study samples are added to the plates then incubated for one hour at room temperature. A goat anti human IgG is used for detection followed by OPD for a colorimetric response. Plates are read at an absorbance of A493 with a reference of A700.

Concentrations from plasma samples are determined from standard curves prepared with known amounts of 1A1 Fab in mouse plasma using a 4/5-parameter algorithm; the range for the Fab and Fab-5K PEG assay is 0.003 to 0.3 µg/mL; the ranges for the Fab-10K PEG assays are 0.006 to 0.2 and 0.04 to 0.4 µg/mL; the ranges for the Fab 20K PEG assays are 0.02-0.4 and 0.04-0.4 µg/mL. Results clearly demonstrate that addition of a PEG molecule and increasing the size of the PEG molecule increases the retention of the Pegylated Fabs in the plasma (77 ng/ml after 96 hours for 20K Pegylated 1A1 Fab) as compared to the non Pegylated 1A1 Fab (not detectable after 24 hours).

B. 1A1 Aβ ELISA Assay

The ELISA is essentially the same as described above for m266. Samples are prepared by diluting plasma into the sample diluents to yield the following: 20% plasma, 0.5 M guanidine, 5 mM Tris pH 8.0, 0.5× protease inhibitor cocktail, 20 µg/ml 1A1, and PBS. The Aβ peptides being measured in these assays are full length Aβ1-40 or Aβ1-42. The colorimetric progression is monitored at 650 nm at 15, 30, and 60 minutes. Results are presented in Table 2 below.

TABLE 2

Pharmacodynamic Results: Average Plasma
Concentration for Aβ 40 (pg/ml)

| Time (h) | 1A1 Fab | 1A1 Fab + 5KD PEG | 1A1 Fab + 10KD PEG | 1A1 Fab + 20KD PEG |
|---|---|---|---|---|
| 1 | 136.8 | 117.1 | 116.3 | 111.2 |
| 4 | 153.6 | 208.2 | 281.6 | |
| 8 | 96.65 | 198.4 | 406.3 | 529.2 |
| 12 | 131.9 | | | |
| 18 | 105.9 | | | |
| 24 | 114.7 | 133.6 | 585.1 | 1243 |
| 48 | 106.8 | 95.12 | 170.7 | 642 |
| 96 | | 88.48 | 113.7 | 177.9 |
| 168 | | 93.96 | 110.8 | 125.4 |
| 240 | | | | 200 |

In a manner similar to m266 Fabs in Example 1, the data from Table 2 demonstrates that humanized Fabs that are covalently attached to a PEG molecule also provide an ideal PK/PD profile allowing for a flexible dosing schedule while preventing the antibody-antigen complex from accumulating in plasma circulation for extended amounts of time.

EXAMPLE 3

Purification of Murine 266 and Humanized 1A1 Fab Analogs

Culture supernatants from cells transfected with mouse 266 Fab or humanized 1A1 Fab and analogs are purified using a two-step chromatography strategy consisting of cation exchange chromatography followed by size-exclusion chromatography using Superdex 75 resin (GE Healthcare). Following harvest, culture supernatant is concentrated using TFF and dialyzed against a 20-fold excess volume of 10 mM sodium acetate pH5 overnight at 4° C. Precipitate is removed by centrifugation and supernatant is loaded over a packed bed of SP sepharose (GE Healthcare) charged with 10 mM sodium acetate pH5. The column is washed with 10 mM sodium acetate pH5 containing successively larger amounts of NaCl until the Fab fragment eluted, at approximately 90 to 110 mM NaCl. Column fractions containing active Fab are identified and pooled. The volume is reduced and buffer exchanged (PBS) using a centrifugal concentration device (Millipore). The final volume is adjusted to 13 ml and loaded over a Superdex 75 sizing column. Fab containing fractions eluting at approximately 50 kD are identified and pooled for further characterization and PEGylation.

EXAMPLE 4

In vitro PEGylation and Characterization

N56C Cysteine on 1A1-Fab purified from cell culture is blocked for PEGylation. Pierce's Reduce-Imm™ Immobilized Reductant beads are used to selectively reduce N56C Cysteine. Reductant beads are extracted from the column provided by the manufacturer and used in a batch mode. ~4 ml of beads are first activated with 8 ml 10 mM DTT in Reduce-IMM Equilibration buffer #1 (sodium phosphate+EDTA, pH 8.0) for 30mins The beads are then washed 3 times with PBS. 18ml of 1A1 N56C Fab at 1.7 mg/ml in PBS pH 7.4 are added to the beads and 10 mM EDTA is added to the mixture. The mixture is rotated and incubated at room temperature for 4-5 hours. Fab is separated from the beads using Handee™ resin separators and the beads are washed with PBS. Fab and washes are combined, and reacted with 5 fold molar excess PEG-maleimide (20 kPEG from NOF; 10 kPEG from Sunbio; SkPEG from Nektar) for one hour. Reaction mixture is dialyzed against 4 L 10 mM sodium acetate buffer pH 5.0 so that the Fab and Fab-PEG can be captured on a SP sepharose column that is equilibrated with 10 mM sodium acetate buffer pH 5.0. Non-reacted Fab and Fab-PEG are eluted with a salt gradient. They are eluted between 50 mM to 70 mM NaCl. The protein is further purified by size exclusion chromatography (Superdex75 column, GE Healthcare) with PBS as the mobile phase. The reduction reaction can be scaled up and down. Similar methods can be used to prepare PEGylated murine 266 Fab N56C.

Samples are analyzed with size exclusion chromatography to confirm the addition of PEG to the Fab. Size exclusion chromatography is performed with TSK G3000PW XL (Tosoh Bioscience) column. The column is run at 0.5 ml/min with PBS plus 0.35 M NaCl at pH 7.4 using an Agilent HP1100 series analytical HPLC operating at 214 nm. In addition, samples are analyzed with SDS-PAGE. 10 µg of purified material is loaded on a 4-12% NuPage® Bis-Tris Gel and stained with SimplyBlue™ SafeStain.

EXAMPLE 5

Measuring Kinetic Constants with Biacore

Biacore® 2000 instrument is also used to measure binding kinetics. The Biacore® utilizes the optical properties of surface plasmon resonance to detect alteration in protein concentration of interacting molecules within a dextran biosensor matrix.

Except as noted, all reagents and materials are purchased from Biacore® AB (Upsala, Sweden). All measurements are performed at 25° C. Samples are dissolved in HBS-EP buffer (150 mM sodium chloride, 3 mM EDTA, 0.005% (w/v) surfactant P-20, and 10 mM HEPES, pH 7.4). Goat anti human kappa antibody is immobilized on flow cells 1 to 4 of a CMS sensor chip at a level of 8000 response units (Ru) using an amine coupling kit.

Binding is evaluated using multiple analytical cycles. Each cycle is performed at a flow rate of 50 µL/minute and consists of the following steps: injection of ~20 µL of an antibody binding composition at 10 mg/mL aiming at a capture of 400-500Rus, injection of 250 µL of Human Abeta (1-40) (starting at 200 nM and using two-fold serial dilutions for each cycle) followed by 20 minutes for dissociation, and regeneration using ~30 µL of 10 mM glycine hydrochloride, pH1.5. Association and dissociation rates for each cycle are evaluated using a "1:1 (Langmuir) binding" model in the BIAevaluation software. Results show that PEGylation at N56C site has little impact on Fab's affinity in binding to human abeta.

EXAMPLE 6

Measuring Equilibrium Constants with KinExA

KinExA analysis is used as an orthogonal approach to measure binding affinity through equilibrium binding analysis due to the slow off-rate of the antigen Fab complex. A KinExA 3000 instrument (Sapidyne Inst. Inc.) is used to measure binding kinetics. Briefly, the antigen is covalently coupled to sepharose beads and the binding of free Fab/Fab-PEG to the beads is detected on the instrument. To measure Kd, individual tubes containing Fab/Fab-PEG (20 pM or 500 pM for 1A1-Fab-20kPEG, 5 pM or 50 pM for 1A1 Fab) with decreasing serially diluted antigen human soluble Abeta (1-40) (0-10 nM), are incubated for 30-50 hrs at 37° C. in PBS containing 1 mg/ml BSA to ensure equilibrium achievement. After the incubation, free Fab/Fab-PEG in each equilibrated sample is determined on the KinExA 3000 according to the manufacturer's instructions. $K_d$ values are determined by n-Curve Analysis using KinExA 3000 software. The results demonstrate that 1A1 Fab binds tightly to human abeta (19 pM), with affinity ~10-fold higher compared to the murine 266 Fab (240 pM). In addition, covalent attachment of 20K PEG at N56C site has no impact on the affinity of 1A1-Fab (12 pM).

EXAMPLE 7

Amyloid Precursor Protein (APP) Binding Analysis Using Cell-based ELISA

To assess cross reactivity of 266 Fabs/mAbs with Abeta precursor APP, HEK 293 cells stably expressing APP (aa 1-751) are used. These cells are created by cloning the APP (1-751) gene into a plasmid containing the neomycin resistance marker. The recombinant plasmid is transfected into HEK 293 and cells are selected in 200 µg/ml G418 to generate an over-expressing stable cell line. For binding assays, 75,000 APP 751 cells are plated in each well of a PDL coated 96-well plate. Following incubation for 2 days in growth media (DMEM F12, 5% FBS, 10 mM Hepes pH7.5, 200 µg/ml G418), liquid is removed and 20 µg/ml of Fab or mAb is added in PBS (with Ca/Mg) containing 10 mg/ml BSA. Binding proceeds for 2 hours at 4 C and cells are washed 3× with 10 mg/ml BSA. A secondary antibody (horseradish peroxidase (hrp) conjugated anti kappa light chain) specific to human or mouse light chain is added in PBS/BSA (Southern Biotech). A dilution of 1:5000 in PBS/BSA is used for anti human light chain and 1:2000 for anti mouse light chain. Following one hour incubation at 4 C, the cells are washed 5× with BSA/PBS. Hrp activity, as a function of Fab/mAb binding to APP, is measured by adding the substrate TMB for 10 minutes. The reactions are transferred to a clear 96-well plate and absorbance at 650 nm is measured. Data indicate that the Pegylated (5 kD, 10 kD), and 20 kD) 1A1-Fab and m266-Fab confer selectivity for Abeta peptide over APP.

We claim:

1. A molecule comprising an antibody Fab fragment with a light chain variable region of SEQ ID NO: 1 and a heavy chain variable region of SEQ ID NO: 2, wherein the said antibody fragment is covalently attached to a 20 kD polyethylene glycol molecule at amino acid position 56 of the heavy chain variable region of the SEQ ID NO: 2.

2. A composition comprising the molecule of claim 1.

3. A composition of claim 2 further comprising a pharmaceutically acceptable carrier.

* * * * *

SEQUENCE LISTING

<160> NUMBER OF SEQ ID NOS: 14

<210> SEQ ID NO 1
<211> LENGTH: 112
<212> TYPE: PRT
<213> ORGANISM: artificial
<220> FEATURE:
<223> OTHER INFORMATION: synthetic construct

<400> SEQUENCE: 1

Asp Ile Val Met Thr Gln Thr Pro Leu Ser Leu Ser Val Thr Pro Gly
1               5                   10                  15

Gln Pro Ala Ser Ile Ser Cys Ser Ser Ser Gln Ser Leu Ile Tyr Ser
            20                  25                  30

Asp Gly Asn Ala Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Ser
                85                  90                  95

Thr His Ser Pro Trp Thr Phe Gly Gly Gly Thr Lys Val Glu Ile Lys
            100                 105                 110

<210> SEQ ID NO 2
<211> LENGTH: 112
<212> TYPE: PRT
<213> ORGANISM: artificial
<220> FEATURE:
<223> OTHER INFORMATION: synthetic construct

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Arg Tyr
            20                  25                  30

Ser Met Ser Trp Val Arg Gln Ala Pro Gly Lys Gly Leu Glu Trp Val
        35                  40                  45

Gly Gln Ile Asn Ile Arg Gly Cys Asn Thr Tyr Tyr Pro Asp Thr Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Phe Trp Gly Gln Gly Thr Leu Val Thr Val Ser Ser
            100                 105                 110

<210> SEQ ID NO 3
<211> LENGTH: 112
<212> TYPE: PRT
<213> ORGANISM: artificial
<220> FEATURE:
<223> OTHER INFORMATION: synthetic construct

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Arg Tyr

```
                    20                  25                  30
Ser Met Ser Trp Val Arg Gln Ala Pro Gly Lys Gly Leu Glu Trp Val
            35                  40                  45

Gly Gln Ile Asn Ile Arg Gly Asn Asn Thr Tyr Tyr Pro Asp Thr Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Phe Trp Gly Gln Gly Thr Leu Val Thr Val Ser Ser
            100                 105                 110

<210> SEQ ID NO 4
<211> LENGTH: 16
<212> TYPE: PRT
<213> ORGANISM: homo sapiens

<400> SEQUENCE: 4

His His Gln Lys Leu Val Phe Phe Ala Glu Asp Val Gly Ser Asn Lys
1               5                   10                  15

<210> SEQ ID NO 5
<211> LENGTH: 15
<212> TYPE: PRT
<213> ORGANISM: homo sapiens

<400> SEQUENCE: 5

His Gln Lys Leu Val Phe Phe Ala Glu Asp Val Gly Ser Asn Lys
1               5                   10                  15

<210> SEQ ID NO 6
<211> LENGTH: 16
<212> TYPE: PRT
<213> ORGANISM: artificial
<220> FEATURE:
<223> OTHER INFORMATION: synthetic construct

<400> SEQUENCE: 6

Ser Ser Ser Gln Ser Leu Ile Tyr Ser Asp Gly Asn Ala Tyr Leu His
1               5                   10                  15

<210> SEQ ID NO 7
<211> LENGTH: 7
<212> TYPE: PRT
<213> ORGANISM: artificial
<220> FEATURE:
<223> OTHER INFORMATION: synthetic construct

<400> SEQUENCE: 7

Lys Val Ser Asn Arg Phe Ser
1               5

<210> SEQ ID NO 8
<211> LENGTH: 9
<212> TYPE: PRT
<213> ORGANISM: artificial
<220> FEATURE:
<223> OTHER INFORMATION: synthetic construct

<400> SEQUENCE: 8

Thr Gln Ser Thr His Ser Pro Trp Thr
1               5

<210> SEQ ID NO 9
```

```
<211> LENGTH: 10
<212> TYPE: PRT
<213> ORGANISM: artificial
<220> FEATURE:
<223> OTHER INFORMATION: synthetic construct

<400> SEQUENCE: 9

Gly Tyr Thr Phe Ser Arg Tyr Ser Met Ser
1               5                   10

<210> SEQ ID NO 10
<211> LENGTH: 16
<212> TYPE: PRT
<213> ORGANISM: artificial
<220> FEATURE:
<223> OTHER INFORMATION: synthetic construct

<400> SEQUENCE: 10

Gln Ile Asn Ile Arg Gly Cys Asn Thr Tyr Tyr Pro Asp Thr Val Lys
1               5                   10                  15

<210> SEQ ID NO 11
<211> LENGTH: 17
<212> TYPE: PRT
<213> ORGANISM: artificial
<220> FEATURE:
<223> OTHER INFORMATION: synthetic construct

<400> SEQUENCE: 11

Gln Ile Asn Ile Arg Gly Asn Asn Thr Tyr Tyr Pro Asp Thr Val Lys
1               5                   10                  15
Gly

<210> SEQ ID NO 12
<211> LENGTH: 3
<212> TYPE: PRT
<213> ORGANISM: artificial
<220> FEATURE:
<223> OTHER INFORMATION: synthetic construct

<400> SEQUENCE: 12

Gly Asp Phe
1

<210> SEQ ID NO 13
<211> LENGTH: 657
<212> TYPE: DNA
<213> ORGANISM: artificial
<220> FEATURE:
<223> OTHER INFORMATION: synthetic construct

<400> SEQUENCE: 13
gacatcgtta tgactcagac tccattgtcc ttgtctgtta ctccaggtca accagcttct      60
atttcctgtt cctcctccca atctttgatc tactccgacg gtaacgctta cttgcactgg     120
tacttgcaaa agcctggtca atccccacaa ttgttgatct acaaggtttc aacagattc      180 tctggtgttc ctgacagatt ttctggttcc ggttccggta ctgacttcac tttgaagatc     240
tccagagttg aagctgagga tgttggtgtt tactactgta ctcagtccac tcattcccca     300
tggacttttg gtggtggtac taaggttgag atcaagagaa ctgttgctgc tccatccgtt     360
ttcattttcc caccatccga cgaacaattg aagtctggta ctgcttccgt tgtttgtttg     420
ttgaacaact tctacccaag agaggctaag gttcagtgga aggttgacaa cgctttgcaa     480
tccggtaact cccaagaatc cgttactgag caagactcta aggactccac ttactccttg     540
```

```
tcctccactt tgactttgtc caaggctgat tacgagaagc acaaggttta cgcttgtgag      600
gttacacatc agggtttgtc ctccccagtt actaagtcct tcaacagagg agagtcc        657

<210> SEQ ID NO 14
<211> LENGTH: 657
<212> TYPE: DNA
<213> ORGANISM: artificial
<220> FEATURE:
<223> OTHER INFORMATION: synthetic construct

<400> SEQUENCE: 14
gaggttcagt tggttgaatc tggtggtgga ttggttaagc ctggtggttc tttgagattg       60
tcctgtgctg cttccggtta cactttctcc agatactcca tgtcctgggt tagacaagct      120
ccaggaaagg gattggagtg ggttggtcaa atcaacatca gaggttgtaa cacttactac      180
ccagacactg ttaagggaag attcactatc tccagagatg actccaagaa cactttgtac      240
ttgcagatga actccttgaa aactgaggac actgctgttt actactgtac tactggtgac      300
tttgggggac agggaacttt ggttactgtt tcctccgctt ctactaaggg accatccgtt      360
tttccattgg ctccatcctc taagtctact tccggtggta ctgctgcttt gggatgtttg      420
gttaaggact acttcccaga gccagttact gtttcttgga actccggtgc tttgacttct      480
ggtgttcaca ctttcccagc tgttttgcaa tcttccggtt tgtactcctt gtcctccgtt      540
gttactgttc catcctcttc cttgggtact cagacttaca tctgtaacgt taaccacaag      600
ccatccaaca ctaaggttga caagaaggtt gaaccaaagt cctctgacaa gactcac        657
```